(12) United States Patent
Handa et al.

(10) Patent No.: US 9,494,580 B2
(45) Date of Patent: Nov. 15, 2016

(54) POLYMER PARTICLE CONTAINING FLUORESCENT MOLECULE AND METHOD FOR PRODUCING THE SAME

(75) Inventors: Hiroshi Handa, Yokohama (JP); Mamoru Hatakeyama, Yokohama (JP); (Continued)

(73) Assignee: TOKYO INSTITUTE OF TECHNOLOGY, Tokyo (JP)

(*) Notice: Subject to any disclaimer, the term of this patent is extended or adjusted under 35 U.S.C. 154(b) by 774 days.

(21) Appl. No.: 13/060,882

(22) PCT Filed: Sep. 10, 2009

(86) PCT No.: PCT/JP2009/004476
§ 371 (c)(1),
(2), (4) Date: Apr. 14, 2011

(87) PCT Pub. No.: WO2010/029739
PCT Pub. Date: Mar. 18, 2010

(65) Prior Publication Data
US 2011/0183355 A1 Jul. 28, 2011

(30) Foreign Application Priority Data
Sep. 11, 2008 (JP) .................... 2008-232832

(51) Int. Cl.
G01N 33/553 (2006.01)
G01N 33/533 (2006.01)
(Continued)

(52) U.S. Cl.
CPC ............... G01N 33/533 (2013.01); C08J 3/12 (2013.01); C08J 3/128 (2013.01);
(Continued)

(58) Field of Classification Search
CPC ............... G01N 33/588; G01N 33/582; G01N 33/533; G01N 33/54313; G01N 33/54346
(Continued)

(56) References Cited

U.S. PATENT DOCUMENTS 6,399,397 B1 * 6/2002 Zarling et al. ............ 436/518
6,548,171 B1 * 4/2003 Barbera-Guillem et al. ................... 428/402.24
(Continued)

FOREIGN PATENT DOCUMENTS

JP     1-103631     4/1989
JP     2001-126909     5/2001
(Continued)

OTHER PUBLICATIONS

Smith et al. "Nanocrystal Synthesis in an Amphibious Bath: Spontaneous Generation of Hydrophilic and Hydrophobic surface coatings". 2008, Angew Chem Int Ed Engl. 47(51): 9916-9921.*
(Continued)

*Primary Examiner* — Mark Shibuya
*Assistant Examiner* — Pensee Do
(74) *Attorney, Agent, or Firm* — Greenblum & Bernstein, P.L.C.

(57) ABSTRACT

Polymer particles are provided which contain fluorescent molecules with high presence ratio in a polymer layer thereof and a method for preparing thereof. Polymer particles are swelled in a non-aqueous solution excluding exclusively water preferably promotes selling of the polymer layer and transfer of the fluorescent molecules to the polymer layer could not protected by water molecules such that much more fluorescent molecule may be introduced into inside of the polymer layer. Furthermore, since the water is added to the reaction system prior to evaporation removal of
(Continued)

the non-aqueous solvent, dry-up of the polymer particles is prevented by the water remained in the reaction system and the polymer particles including fluorescent molecules with high presence ratio of the fluorescent molecules preferably keep high dispersibility using the above described procedures.

5 Claims, 8 Drawing Sheets

(75) Inventors: Satoshi Sakamoto, Yokohama (JP); Yusuke Mochizuki, Yokohama (JP); Shintaro Kawada, Yokohama (JP)

(51) Int. Cl.
    *C08J 3/12*           (2006.01)
    *G01N 33/543*     (2006.01)
    *H01F 1/06*          (2006.01)
    *H01F 1/09*          (2006.01)

(52) U.S. Cl.
    CPC .......... *G01N 33/54326* (2013.01); *H01F 1/06* (2013.01); *H01F 1/09* (2013.01); *C08J 2327/12* (2013.01)

(58) Field of Classification Search
    USPC ......................................... 436/501, 518, 526
    See application file for complete search history.

(56) References Cited

U.S. PATENT DOCUMENTS

2006/0131542 A1*   6/2006   Weng et al. ............. 252/301.16
2010/0323457 A1    12/2010   Handa et al.
2011/0006245 A1     1/2011   Handa et al.

FOREIGN PATENT DOCUMENTS

| JP | 2006-88131 | 4/2006 |
| JP | 2007-308548 | 11/2007 |
| JP | 2008-127454 | 6/2008 |
| WO | WO2007/029980 | * 3/2007 |

OTHER PUBLICATIONS

Merriam Webster dictionary Feb. 4, 2016.*
English language translation of International Preliminary Report on Patentability, Mailed Apr. 14, 2011.

* cited by examiner (a)

(b)

POLYMER PARTICLE CONTAINING FLUORESCENT MOLECULE AND METHOD FOR PRODUCING THE SAME

TECHNICAL FIELD

The present invention relates to polymer particles containing fluorescent molecule, and more particularly relates to polymer particles which contain fluorescent molecules with high presence ratio in a polymer layer thereof and a method for preparation thereof.

BACKGROUND ART

Recently, extended applications of magnetic particles as marker materials in a biosensing field have been variously studied. In this regards, Japanese Patent (Laid Open) No. 2006-88131 (Patent Literature 1) already filed by the same applicant discloses polymer magnetic particles with high dispersibility required for markers while keeping magnetic response properties of magnetic particles. As further developments, Japanese Patent (Laid Open) No. 2008-127454 (Patent Literature 2) already filed by the same applicant discloses multi-functional polymer magnetic particles having a function as a fluorescent marker and the magnetic response performance by incorporating fluorescent molecules within the polymer layer covering the magnetic particle. Now for the polymer magnetic particles containing fluorescent molecule, introduction of much fluorescent molecules to the coating polymer layer may be desired so as to realize fluorescence luminance detectable by a known fluorescence detector.

PRIOR ART LITERATURE

Patent Literature

PATENT LITERATURE 1: Japanese Patent (Laid-Open) No. 2006-88131
PATENT LITERATURE 2: Japanese Patent (Laid-Open) No. 2008-127454

SUMMARY OF INVENTION

Object to be Solved by Invention

The present invention has been completed regarding to the above described prior art and an object of the present invention is to provide polymer particles including fluorescent molecules with high presence ratio in the polymer layer and a method for preparation thereof.

Means for Solving Object

The inventors have been paid much efforts for the method to introduce much more fluorescent molecules in the polymer layer on the polymer particle and have succeeded in enlarging significantly the presence ratio of the fluorescent molecules. That is, the inventors have found that selling the polymer particles in a non-aqueous solvent excluding exclusively water preferably promotes selling of the polymer layer and transfer of the fluorescent molecules to the polymer layer could not protected by water molecules such that much more fluorescent molecule may be introduced into inside of the polymer layer. Furthermore, the inventors have found that addition of water to the reaction system prior to evaporation removal of the non-aqueous solvent prevents dry-up of the polymer particles by the water remained in the reaction system after the evaporation removal of the non-aqueous solvent. The inventors have reached to the present invention by discovering that the polymer particles including fluorescent molecules with high presence ratio of the fluorescent molecules preferably keep high dispersibility using the above described procedures.

As described above, the present invention may provide a method and the method may comprise the steps of:

swelling a coating polymer layer of polymer magnetic particles in a non-aqueous solvent dissolving therein fluorescent molecules and absorbing the fluorescent molecules inside the swelled coating polymer layer;

adding water to the non-aqueous solvent in which the polymer magnetic particles absorbing the fluorescent molecules; and removing the non-aqueous solvent by evaporation.

In the present invention, In the present method, the non-aqueous solvent may have affinity with water and may have a lower boiling point and a higher vapor pressure than those of water.

According to the present invention, a polymer magnetic particles may be provided and the fluorescent molecules may be introduced inside a coating polymer layer and the polymer magnetic particles containing fluorescent molecule may contain at least 100 nmol of the fluorescent molecules per 1 mg of the polymer particles containing fluorescent molecule. In the present invention, the coating polymer layer may be formed by a polymer consisting of a monomer component selected from styrene. Further according to the present invention, the fluorescent molecules are selected from rare earth metal chelate complexes and the rare earth metal consisting of the rare earth metal chelate complexes may be selected from the group consisting of Europium, Samarium, Terbium and Dysprosium.

Further according to the present invention, a method for preparing a polymer magnetic particles containing fluorescent molecule may be provided and the method may comprise the steps of:

removing water by solvent, substitution from aqueous dispersion of polymer magnetic particles with a non-aqueous solvent and then swelling a coating polymer layer of polymer magnetic particles in a non-aqueous solvent dissolving therein fluorescent molecules and absorbing the fluorescent molecules inside the swelled coating polymer layer;

adding water to the non-aqueous solvent in which the polymer magnetic particles absorbing the fluorescent molecules; and removing the non-aqueous solvent by evaporation. Further according to the present invention, a polymer magnetic particles containing fluorescent molecule, the fluorescent molecules being introduced inside a polymer layer, the polymer magnetic particles containing fluorescent molecule contain at least 100 nmol of the fluorescent molecules per 1 mg of the polymer particles containing fluorescent molecule.

As described hereinabove, the present invention may provide polymer particles having high dispersibility while containing fluorescent molecule with high presence ratio in the polymer layer and the method for preparation thereof.

EMBODIMENT FOR PRACTICING INVENTION

Figure 1:
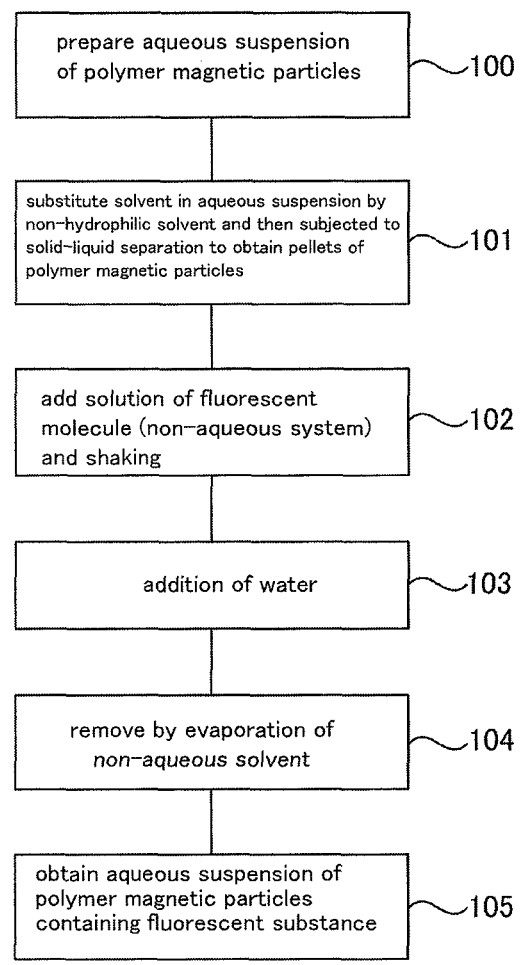
FIG. 1 shows a flowchart of a preparation process of polymer magnetic particles containing fluorescent molecule according to an embodiment of the present invention.

Hereinafter, the present invention will be explained using embodiments depicted in drawings; however, the present invention must not limited to the embodiments described in the drawings.

Now, the present invention particularly explained by using the practical example in which the fluorescent molecules are introduced into a coating polymer layer of the polymer magnetic particles having magnetic responsibility. FIG. 1 shows a flowchart of a preparation method of the polymer magnetic particles containing fluorescent molecule according to the present embodiment. In the explained embodiment, first the water dispersion solution of the polymer magnetic particles is prepared in the process 100. The process 100 may use according to the disclosure of Japanese Patent (Laid-Open) No. 2006-88131 (Patent Literature 1) filed formerly by the present applicant(s) the method described herein below:

First, a surface active agent is adsorbed to hydrophilic magnetic particles such as ferrite followed by hydrophobic treatment and then the monomer solution which is able to polymerize via. radical addition polymerization such as styrene or glycidyl methacrylate and a surface active agent having nonionic hydrophilic group are added to the ferromagnetic particles followed by addition and mixing of adequate amounts of water followed by sonication to prepare emulsion. The emulsion solution such prepared is heated to 60-80 Celsius degrees and then a hydrophilic initiator is added thereto to polymerize the monomers via. an emulsion polymerization. At last, the surface active agent may be rinsed to remove from the emulsified particles after the polymerization such that water dispersion solution of the polymer magnetic particles which are formed by coating the magnetic particles by polymer may be obtained.

In the subsequent process step 101, the solvent of the water dispersion solution of the polymer magnetic particles, i.e, water is replaced with non-aqueous solvent then solids are separated. The process 101 may be for example performed according to the following steps: First the water is removed from the water dispersion solution of the polymer magnetic particles by using a centrifugal separator to subject solid-solution separation and then alcohol such as methanol is added to the residual pellets followed by further solid-solution separation and the above routine is repeated for several times to complete this step. The above alcohol rinsing removes hydrophilic materials included in the coating polymer layer such that the swelling of the coating polymer layer may be promoted.

In the subsequent process step 102, the solution of fluorescent molecules dissolved into non-aqueous solvent (hereafter referred to fluorescent molecule solution) is added to the pellets of the polymer magnetic particles obtained by the solid-solvent separation of the step 101 and then the mixture is subjected to shaking. In the step 102, the coating polymer layers of the polymer magnetic particles are swelled by the non-aqueous solvent of the fluorescent molecular solution such that the fluorescent molecules are absorbed inside the swelled polymer together with the non-aqueous solvent.

Here, in the present embodiment, the fluorescent molecules introduced into the coating polymer layer may include such as, for example, rare earth metal chelate complexes. Rare earth metals included in the rare earth metal chelate complexes may include Samarium, Terbium, and Dysprosium as well as Europium.

In the described embodiment, solvent replacement has been performed in the former step 101 and then the water is removed from the reaction system of the step 102. As the result, the swelling of the coating polymer layer is preferably promoted and the migration of the fluorescent molecules into the coating polymer layer could not be prevented by the water molecules so that much more fluorescent molecules may be introduced into the inside of the coating polymer layer. According to the present embodiment, the non-aqueous solvent used as the fluorescent molecule solution and as the solvent for swelling the coating polymer layer may be preferably selected from organic solvents which have affinity with water and have lower boiling point, i.e, higher vapor pressure than that of water. For example in the present embodiment, acetone may be used as the non-aqueous solvent which includes a hydrophilic group and has the boiling point of 56.5 Celsius degrees.

In the step 102, preferably after the migration of the fluorescent molecules to the coating polymer layer becomes saturated, the water is added to the above reaction system in the step 103. The water to be added may preferably be pure water such as distilled water or milliQ water. The amount of the water to be added may preferable be equal to the amount of the non-aqueous solvent of the above reaction system.

Lastly, in the step 104, the non-aqueous solvent is removed from the reaction system of the step 103 by evaporation. The evaporation removal of the non-aqueous solvent may be conducted by the method such as, for example, reduced pressure treatment, heat treatment, or heating at the reduced pressure under the condition that only the non-aqueous solvent having lower boiling point than water evaporate. As the result, the non-aqueous solvent absorbed in the coating polymer layer is removed and only the fluorescent molecules are remained in the coating polymer layer. Here, because the water added in the step 103 is present in the reaction system, the polymer magnetic particles to which the fluorescent molecules are introduced may be prevented from the dry-up thereof so that high dispersibility of the polymer magnetic particles may preferably be maintained. Finally, the water emulsion of the polymer magnetic particles containing fluorescent molecule with high presence ratio may be prepared.

According to the above described procedures, the fluorescent molecules at least 100 nmol, preferably not less than 150 nmol, more preferably not less than 200 nm, desirably not less than 250 nmol per 1 mg of the polymer magnetic particles containing fluorescent molecule may be introduced therein. In other words, in the present embodiment, the fluorescent molecules at least $4.0 \times 10^5$, preferably not less than $6.0 \times 10^5$, more preferably not less than $8.0 \times 10^5$, and desirably not less than $1.0 \times 10^6$ molecules per one polymer magnetic particle containing fluorescent molecule may be introduced therein so that the fluorescence luminance sufficiently used as the marker may be attained.

As described above, the polymer magnetic particles containing fluorescent molecule may be provided in the condition with keeping high dispersibility. That is to say, an excellent quantitative performance may be ensured according to the present preparation method. In addition, much more amounts of the fluorescent molecules may be introduced inside the polymer in the perfectly packed form according to the present preparation method so that the present polymer magnetic particles containing fluorescent molecule may provide stable fluorescence of high luminance in various circumstances such as in cells or in living bodies without affected by outer circumstance.

The polymer magnetic particles of the present embodiment may be bound with ethylene glycol diglycidyl ether (EGDE), buthylene glycol diglycidyl ether, polyethylene glycol (PEG) on the surface of the coating polymer layer in order to improve binding properties to bioactive substances and the above method for introducing the fluorescence molecules may be similarly applied to the polymer magnetic particles in the condition that spacer molecules are combined thereto.

As described above, the present invention has been described using the embodiment that the fluorescent molecules are introduced into the coating polymer layer of the polymer magnetic particles which are formed by the hydrophilic magnetic particles such as ferrite as a core; however, the scope of the present invention relates to a general method for introducing the fluorescent molecules into particle shaped polymers. Therefore, it is noted that the present invention should not be understood by limiting the objective of the fluorescent molecules introduction only to the polymer magnetic particles. That is to say, the present invention may be possible to incorporate the fluorescent molecules with high presence ratio as described above within the polymer particles by applying the processes after the step 102 to aqueous emulsion of known polymer particles which do not include magnetic particles and are prepared by known method such as, for example, emulsion polymerization or suspension polymerization and this scope of the present invention will be understood by a person with ordinary skill in the art.

EXAMPLE

Now, the present polymer magnetic particles containing fluorescent molecule will be explained more practically by using examples; however, the present invention should not be limited to the examples explained hereinafter.

<Preparation of Edge Modified Polymer Magnetic Particles>

$FeCl_2$ aqueous solution was added to NaOH aqueous solution (1M) and the oxidization treatment by $NaNO_3$ was applied followed by keeping at a constant temperature to precipitate ferrite particles with an average particle size of 40 nm. To the 150 mg of this ferrite suspension NaOH aqueous solution of 10-undecenoic acid was added to adsorb the undecenoic acid to the saturation thereof and the residual NaOH solution of 10-undecenoic acid was rinsed and removed to obtain hydrophobic ferromagnetic particles.

To the above hydrophobic ferromagnetic particles, aqueous solution of a nonionic surface active agent having PEO chains Emulgen 1150-70 (Kao Co. Ltd.) 0.3 g was added followed by sonication to make the particles hydrophilic again by adsorbing the nonionic surface active agent to the hydrophobic ferromagnetic particles and the ferromagnetic particles were dispersed in water.

Next, the monomer mixture which includes styrene (monomer) 2.7 g, GMA (glycidyl methacrylate, monomer) 0.3 g, AIBN (azobis-isobutyronitryl, initiator) 0.025 g, DVB (divinyl benzene, crosslinker) 0.08 g, and diethyl ether 2.5 g, was added to the colloidal dispersion solution and the mixture was subjected to the sonication to obtain the emulsified solution.

Further next, water was added to this emulsified solution until the total amount of the mixture was 125 g and then applied sonication followed by heating under stirring at 350 rpm. After 20-30 minutes the temperature was raised to 70 Celsius degrees, the aqueous solution prepared by dissolving a water soluble initiator V-50 (Wako Pure Chemical Industries, Ltd.) 50 mg in water 5 ml was added and the polymerization reaction was conducted for 12 hours. The obtained particles by the emulsion polymerization were rinsed to obtain the aqueous suspension of the polymer magnetic particles which were the ferrite particles were coated by the polymer.

Furthermore, the polymer magnetic particles prepared by the above procedures was modified by binding ethylene glycol diglycidyl ether (EGDE) as the spacer. First, $NH_4OH$ aqueous solution was added to the slurry of the particles in order to introduce the amino group and the mixture was reacted under controlled pH with HCl aqueous solution to introduce the amino groups by opening the epoxy groups in GMA.

Next, the amino groups of polymer coated ferrite particles were bound with the epoxy groups of EGDE to the open-ringed amino groups of the polymer magnetic particles by charging excess amounts of EGDE and the stirred under controlled pH with NaOH. After the reaction, water rising was applied thereto by using a magnetic separation operation to obtain aqueous suspension of the polymer magnetic particles modified by EGDE.

<Introduction of Fluorescent Molecules>
(Preparation of Fluorescent Molecule Solution)

$Eu(TTA)_3(TOPO)_2$ complex (Eu complex which was coordinated with tenoyltri-fluoro-acetone (1.1 mg was added to acetone 0.22 g to prepare the acetone solution of the fluorescent molecules.

(Alcohol Rinsing)

In order to promote the swelling of the polymer layer of the polymer magnetic particles, alcohol rinsing was applied to the polymer magnetic particles to remove hydrophilic substances adsorbed to the polymer layer. Particularly, the aqueous suspension 1 mg of the polymer magnetic particles prepared by the above procedures was subjected to solid-liquid separation by a centrifugal separator to remove water and methanol was added to the residual pellets and the mixture was dispersed and then was subjected to the solid-liquid separation again by the similar procedures; such procedures were repeated for several times. In the last solid-liquid separation, the residual pellets after removal of the methanol were used in the following examples and comparative examples.

Example 1

To the pellets obtained by the above procedures, the acetone solution containing 1.08 g of the fluorescent molecule was added to disperse the polymer magnetic particles in the acetone solution. The obtained acetone solution was shaken for 1 hour at a room temperature and then, milliQ water was added to the acetone solution. The milliQ water was added in the same amount with the acetone solution. Then, the acetone was removed by vacuum heating at 60 Celsius degrees to obtain the aqueous dispersion of the polymer magnetic particles.

Comparative Example 1

To the pellets obtained by the above procedures, milliQ water was added to disperse the polymer magnetic particles, Next, the acetone solution including 1.08 μmol of the fluorescent molecules was added and mixed to the aqueous suspension. Here, the acetone solution of the fluorescent molecules was added in the same amount to the amount of the milliQ water. Lastly, the mixed solution was shaken for 1 hour at the room temperature and the acetone was removed by vacuum heating at 60 Celsius degrees to obtain the aqueous dispersion of the polymer magnetic particles.

Comparative Example 2

To the pellets obtained by the above procedures, the acetone solution including 1.08 μmol was added and mixed to the aqueous suspension. The acetone solution was shaken for 1 hour at the room temperature and the acetone was removed by vacuum heating at 60 Celsius degrees to obtain the aqueous dispersion of the polymer magnetic particles.

<Examination of Dispersibility>

For each of the aqueous suspension obtained Example 1 and Comparative Example 1, the solid-liquid separation was applied by using the centrifugal separator and the obtained pellets were rinsed by dispersing in 0.1% NP-40 (surface active agent "NONIDET" P-40, supplier; NACALAI TESQUE, INC.) solution and then were subjected to the evaluation of dispersibility after dispersing in the water. In addition, the powdery polymer magnetic particles obtained in Comparative Example 2 was similarly added with the solution of 0.1% NP-40 to try to disperse in water. The evaluation of the dispersibility was made by results of measurements of weight converted distribution of the particle diameters using a dynamic light scattering method. For measurements of the weight converted distribution of the particle diameter, FPAR-1000 (OTSUKA ELECTRONICS CO., LTD.) was used.

Figure 2:
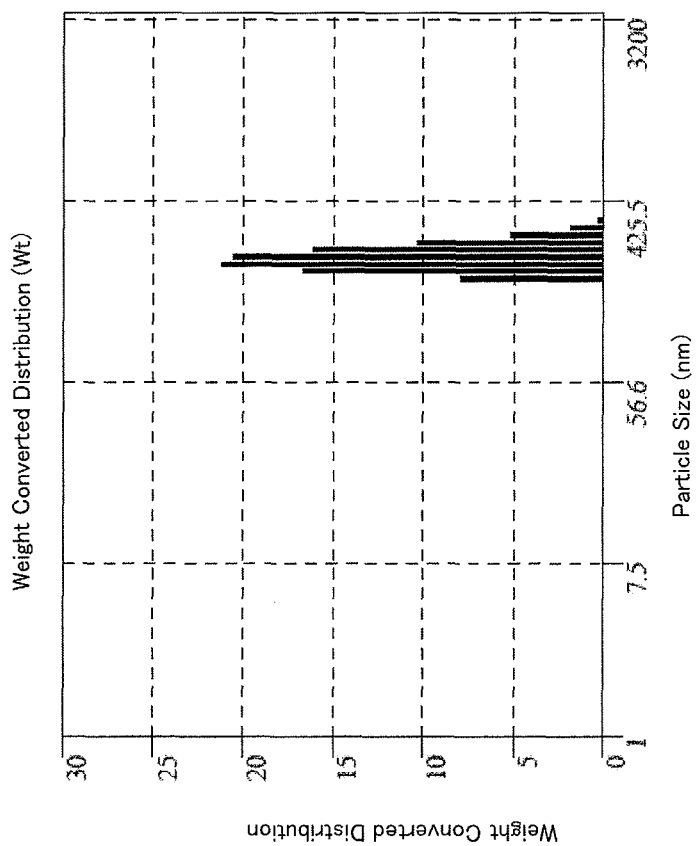
FIG. 2 shows a result of measurement of weight-converted distribution of particle diameters of the polymer magnetic particles containing fluorescent molecule according to Example 1.
Figure 3:
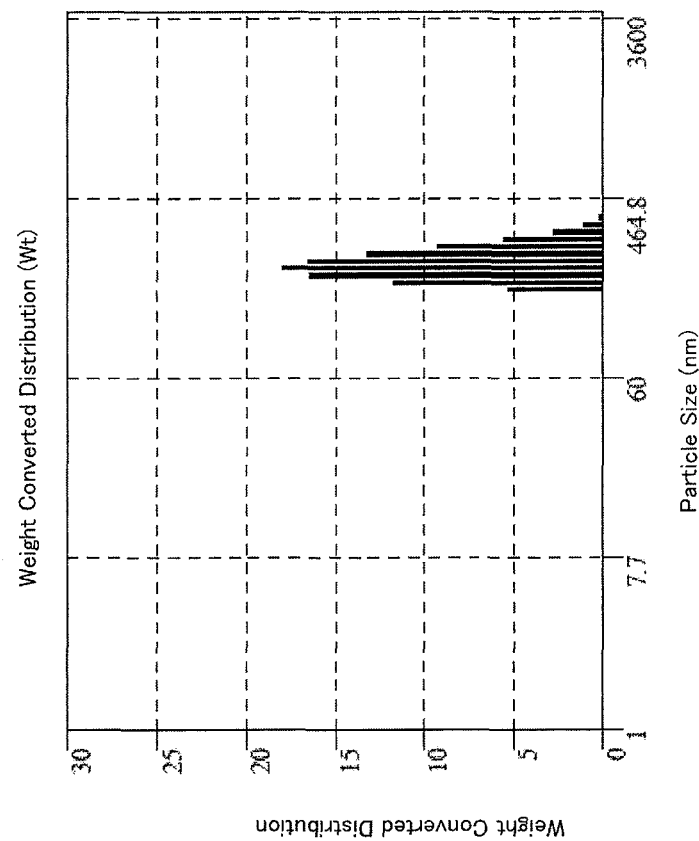
FIG. 3 shows a result of measurement of weight-converted distribution of particle diameters of the polymer magnetic particles containing fluorescent molecule according to Comparative Example 1.
Figure 4:
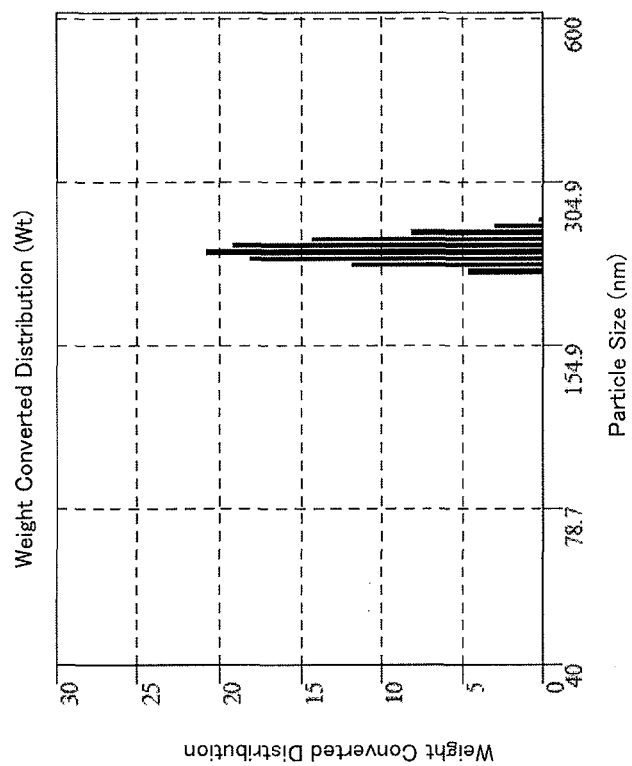
FIG. 4 shows a result of measurement of weight-converted distribution of particle diameters of the polymer magnetic particles prior to introduction of fluorescent molecules.

FIG. 2 shows the result of measurement of the weight converted distribution of the particle diameters for the polymer magnetic particles containing fluorescent molecule of Example 1 and FIG. 3 shows the result of measurement of the weight converted distribution of the particle diameters for the polymer magnetic particles containing fluorescent molecule of Comparative Example 1. FIG. 4 shows the result of measurement of the weight converted distribution of the particle diameters for the polymer magnetic particles prior to the introduction of the fluorescent molecules. The polymer magnetic particles prior to the introduction of the fluorescent molecules showed a single peak distribution as shown in FIG. 4 and both of Example 1 and Comparative Example 1 also shows a single peak as their results shown in FIG. 2 and FIG. 3 which were similar to the result shown in FIG. 4; The average particle sizes were in any cases to be about 220 nm and then it was confirmed that single particle dispersion was maintained after the introduction of the fluorescent molecules. Though the inventors tried to measure the specimen of Comparative Example 2, the sample polymer magnetic particles were significantly aggregated such that dispersion into water was impossible and then the measurement itself was impossible. From the result of the Example 1, it was shown that the present polymer magnetic particles containing fluorescent molecule had sufficient dispersibility. This fact may ensure excellent quantitative performance in the usage for sensing markers.

<Examination of Introduction Amounts of Fluorescent Molecules>

Next, for each of Example 1 and Comparative Example 1, the introduction amounts of $Eu(TTA)_3(TOPO)_2$ complex. Particularly, the Europium complex was exuded from the polymer magnetic particles introduced with the fluorescent molecules using acetone and the exuded Europium was subjected to quantitative analysis using an Atomic Emission Spectrometry (ICE-OES, Leeman Labs, Inc U.S.A. Apparatus Name: Prodigy ICP). The results of the quantitative measurements are shown in Table 1 as follows:

TABLE 1

|  | Europium amounts (nmol) per polymer magnetic particles 1 mg | Europium complex numbers per one polymer magnetic particle |
| --- | --- | --- |
| Example 1 | 386 | $1.41 \times 10^6$ |
| Compatative Example 1 | 55.1 | $2.01 \times 10^5$ |

As shown in Table 1 above, Europium of 55.1 nmol per 1 mg of the polymer magnetic particles in Comparative Example 1. This value, when translated assuming the weight of one polymer magnetic particle to be $6.07 \times 10^{-15}$ g, means that the Europium complexes of $2.01 \times 10^5$ per one polymer magnetic particle were introduced. Here, the weight of one polymer magnetic particle was derived by the following procedures: the volume ratio of the polymer layer in the present polymer magnetic particle was decided to be about 62% by a thermal analysis. From the specific weight of magnetite (5.3 g/cm$^3$) and the specific weight of polymer (1.0 g/cm$^3$), the specific weight of the present polymer magnetic particles was estimated to be 1.45 g/cm$^3$. On the other hand, the particle size of the polymer magnetic particle of the present invention was determined to be about 200 nm and hence the weight per one polymer magnetic particle was estimated to be $7 \times 10^{-15}$ g.

On the other hand, in Example 1, it was determined that 386 nmol of Europium was introduced to the polymer magnetic particle per 1 mg of the polymer magnetic particles. This means that $1.41 \times 10^6$ Europium complexes were introduced into one polymer magnetic particle such that it was determined that in Example 1 the introduction amounts of the fluorescent molecules were increased to be about 7 times than the amounts of Comparative Example 1.

<Examination of Introduction State of Fluorescent Molecules>

Furthermore, with respect to the polymer magnetic particles prepared in Example 1, it was examined by following procedures that the fluorescent molecules ($Eu(TTA)_3(TOPO)_2$ complex) is introduced in the form in which the molecules were closely enclosed into the polymer rather than attached to the surface thereof.

(pH Dependence of Fluorescence Intensity)

Each of dispersion solutions (hereafter referred to fluorescent polymer magnetic particle dispersion) of the polymer magnetic particles prepared in Example 1 in four pH solutions of four buffers (acetic acid buffer, boric acid+ sodium hydroxide buffer, phosphoric acid buffer, Hepes- NaOH buffer) was prepared. Each of the fluorescent polymer magnetic particle dispersions was prepared to be particle concentrations of 20 µg/ml.

On the other hand, micellar $Eu(TTA)_3(TOPO)_2$ complex was dispersed in the above four kinds of pH solutions to prepare Comparative Examples (hereafter referred to sole Europium dispersion). Here, each of the sole Europium dispersion was prepared to their concentration to be 1 nmol/ml.

Each of the fluorescent polymer magnetic particle dispersions and sole Europium dispersion prepared by the above procedure was measured their fluorescence luminance by using a fluorescence spectrophotometer LS-55 (Perkin Elmer). In the measurements, the excitation was set to be 340 nm and the emission was set to be 550-700 nm; the fluorescence intensity at 618 nm was adopted as the fluorescence intensity. Slit widths were 10.0 nm both for the excitation and emission.

Figure 5:
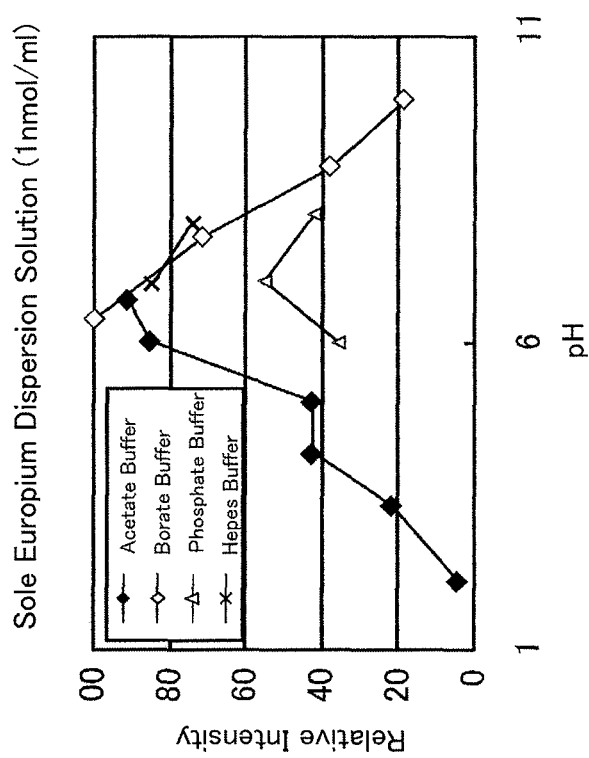
FIG. 5 shows a result of fluorescence measurement for sole europium dispersion solution.

FIG. 5 shows the results for the measurements of the fluorescence intensity about the sole Europium dispersion. As shown in FIG. 5, strong fluorescence was observed at pH of the neutral for the sole Europium dispersion in all buffers; however, the fluorescence intensities decreased promptly at the other pH range and it was found that the fluorescence intensity of $Eu(TTA)_3(TOPO)_2$ complex was influenced strongly by pH of the outer circumstance.

Figure 6:
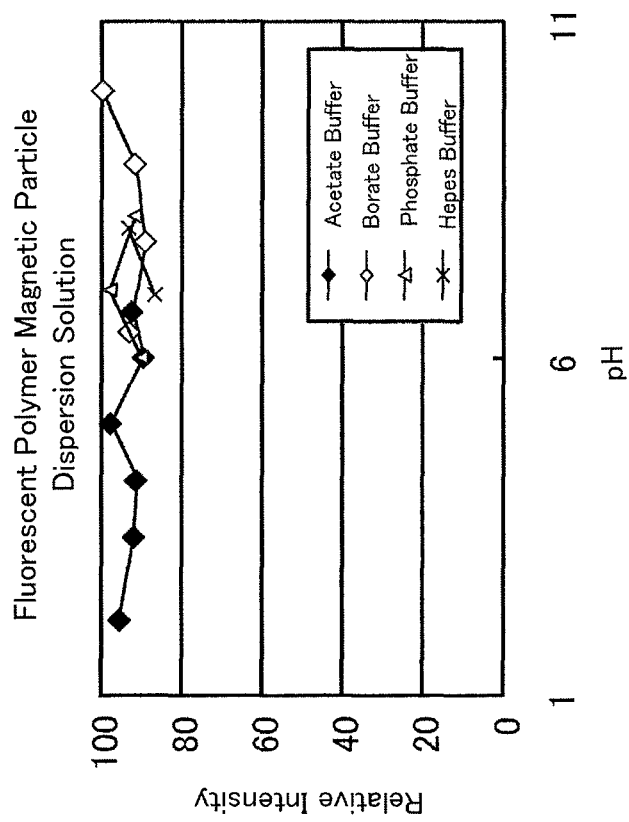
FIG. 6 shows a result of fluorescence strength for fluorescent polymer magnetic dispersion solution.

On the other hand, FIG. 6 shows the result for measurements of fluorescence intensity about the fluorescent polymer magnetic particle dispersion. As shown in FIG. 6, the fluorescent polymer magnetic particle dispersion maintains the strong fluorescence intensities at all of the pH range and the fluorescence intensities thereof did not affected by pH of the outer circumstance.

(Quencher Concentration Dependence on Fluorescence Intensity)

The fluorescent polymer magnetic particles dispersion (pH 7.95) and sole Europium dispersion (pH 7.95) prepared by the above described procedure were added with EDTA which is known as a fluorescence quencher and then the fluorescence intensity was measured in the similar condition described above. Now, EDTA concentrations were set to five conditions (0 mM, 0.1 mM, 0.3 mM, 1 mM, and 3 mM).

Figure 7:
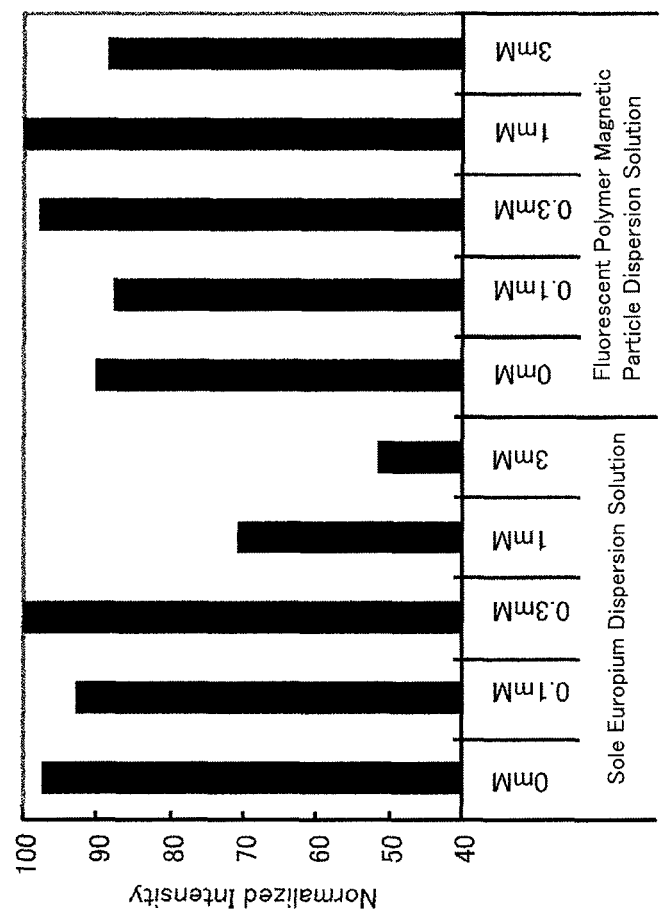
FIG. 7 shows relations of respective fluorescence strength and ethylenediamine tetra acetic acid (EDTA) concentrations between fluorescent polymer magnetic dispersion solution and europium dispersion solution.

FIG. 7 shows relations between the fluorescence intensities and the EDTA concentrations each for fluorescent polymer magnetic particle dispersion and sole Europium dispersion. As shown in FIG. 7, the fluorescence starts to decrease about the EDTA concentration of 1 mM in the sole Europium dispersion and the fluorescence intensity decreased to 50% at the EDTA concentration 3 mM. On the other hand, the decrease of fluorescence intensity was not observed in the fluorescent polymer magnetic dispersion with respect to increment of the EDTA concentration as shown in FIG. 7.

The above measurement results indicated that the Europium complex introduced into the fluorescent polymer magnetic particles prepared in Example 1 did not affected by the external circumstance. This fact suggested that the Europium complexes were introduced in the polymer being enclosed closely rather than being attached to the surface of the polymer.

From the results of Example described above, much more fluorescence molecules might be enclosed perfectly and closely inside of the polymer in the polymer magnetic particles containing fluorescent molecule of the present invention. This fact suggests that the polymer magnetic particles containing fluorescent molecule ensure to supply high luminance fluorescence stably without being affected by the outer circumstance.

Next, immunostaining (fluorescence immunostaining method) of a mammary gland CNB specimen by immunofluorescence method was performed using the polymer magnetic particle containing fluorescent molecule prepared in Example 1.

(Immobilization of Anti-EGFR Antibody to Polymer Magnetic Particles Containing Fluorescent Molecule)

The polymer magnetic particles modified with EGDE prepared in Example 1 was reacted with 3.0 M $NH_4OH$ for 24 hours at 70 Celsius degrees to introduce the amino groups to terminal epoxy groups of EGDE and then was reacted in 0.5 M dry succinic acid DMF solution for 12 hours (room temperature) to introduce carboxyl groups on the polymer magnetic particles. To these polymer magnetic particles the Europium complexes were introduced using the similar method with Example 1 to prepare carboxylated polymer magnetic particles containing fluorescent molecule were prepared.

To 1 mg of the carboxylated polymer magnetic particles containing fluorescent molecule prepared by the above procedure, 200 µl of milliQ solution (20 mg/ml) of EDC (1-ethyl-3-(3-dimethyl aminopropyl) carbodiimide) was added and the mixture was shaken for 30 min. at 4 Celsius degrees to activate carboxyl groups followed by quickly rinsing using the centrifugal separation with milliQ cooled on 500 µl of ice and immobilization buffer for the antibody on the particle each for one time. Subsequently, the solution of anti-EGFR antibody of 50 µg equivalence dissolved in 50 µl of the immobilization buffer for the antibody on the particle was added. After the shaking for 2 hours at 4 Celsius degrees, it was performed by addition of 5 µl of 1 M ethanol amine followed by shaking for one day and one night at 4 Celsius degrees. Lastly, five times rinsing with 1 ml of the immobilization buffer for the antibody on the particle were performed and the resulted anti-EGFR antibody immobilized polymer magnetic particles containing fluorescent molecule were stored in dark at 4 Celsius degrees.

(Immunostaining Using Anti-EGFR Antibody Immobilized Polymer Magnetic Particles Containing Fluorescent Molecule)

A paraffin slice of the mammary gland CNB specimen was put on a slide glass and then paraffin removal treatment by xylene, hydrophilization treatment by methanol, and rinse with running water (15 min) were applied thereto. Further to the above sample, an antigen activation treatment (room temperature, 30 min) with DAKO Proteinase K (0.4 mg/ml/0.05 M TBS pH 7.5-7.7) was applied and then applied another rinsing with running water was applied followed by a blocking treatment with 5% BSA (20 min).

Dispersion of the anti-EGFR antibody immobilized polymer magnetic particles containing fluorescent molecule prepared by the above procedure (dispersion solvent: 10 mM Hepes-NaOH (pH 7.9), 50 mM KCl, 1 mM EDTA, 0.1% (w/v) Tween 20) was dropped to the above sample and then a neodymium magnet was placed at back side for 10 min. Then, after the sample was rinsed by TBS, it was sealed by hydrophilic sealant.

Here, a tissue slice of the same mammary gland CNB specimen was prepared by applying immunostaining with a immunoperoxidase protocol (staining solution: Mayer7s Hematoxylin).

Figure 8:
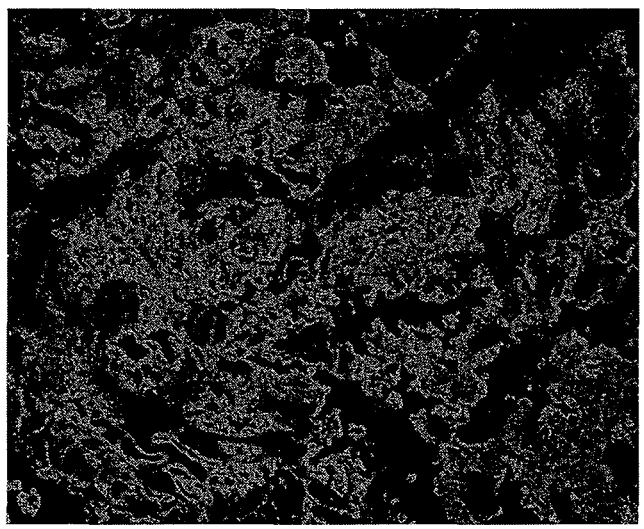
FIG. 8 shows photographic images of immunostaining by the polymer magnetic particles containing fluorescent molecule of Example 1.
Figure 8:
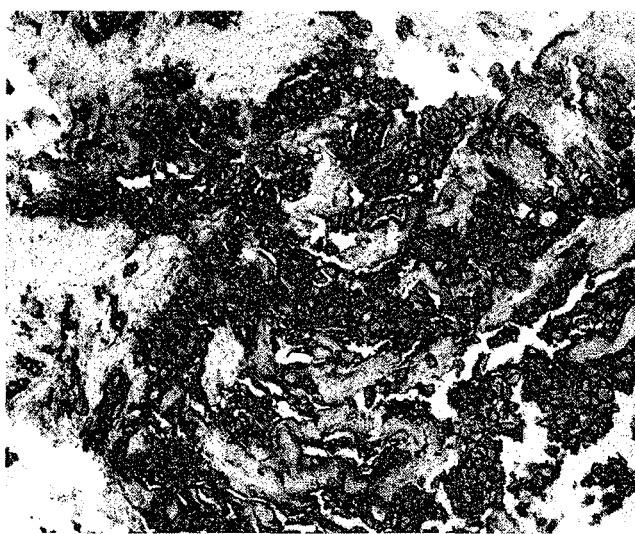

FIG. 8(a) shows a fluorescence microscope photograph of the sample by using the polymer magnetic particles containing fluorescent molecule of Example 1 and FIG. 8(b) shows a fluorescence microscope photograph of the reference sample which was applied with the immunostaining using the immunoperoxidase protocol. As shown in FIG. 8, it was confirmed that the immunostaining using the polymer particles containing fluorescent molecule of the present invention provided the immunostaining of cancerous positions with equal contrasts to those of the reference sample.

From the results of Examples described hereinabove, it has been confirmed that the necessary and sufficient fluorescence luminance may be supplied when the polymer magnetic particles containing fluorescent molecule of the present invention is applied to the fluorescence marker for the biosensing with using the affinity reaction.

INDUSTRIAL APPLICABILITY

As explained hereinbefore, the present invention may provide the polymer particles which contain much more fluorescent molecules inside the polymer layer and a method for preparation thereof. The polymer particles containing fluorescent molecule may function stably as the fluorescence marker with high luminance and hence, it may be expected to further applicative extensions as useful marker materials in the biosensing fields.

The invention claimed is:

1. A polymer magnetic particle comprising:
   a magnetic core;
   a coating polymer layer on the magnetic core; and
   a fluorescent compound being soluble in a non-aqueous solvent as a non-crystal state, the fluorescent compound being adsorbed and localized in the coating polymer layer as the non-crystal state at a concentration at least 100 nmol per 1 mg of the polymer magnetic particles.

2. The polymer magnetic particle of claim 1, wherein the fluorescent compound possesses hydrophobicity.

3. The polymer magnetic particle of claim 2, wherein the fluorescent compound further comprises a rare earth element.

4. The polymer magnetic particle of claim 3, wherein the rare earth element is selected form the group consisting of europium, samarium, terbium, and dysprosium.

5. The polymer magnetic particle of claim 1, wherein the fluorescent compound is a rare earth metal chelate complex.

\* \* \* \* \*